(12) United States Patent  
Metzger et al.

(10) Patent No.: US 8,210,176 B2
(45) Date of Patent: *Jul. 3, 2012

(54) METHOD AND SYSTEM TO DECREASE INTRACRANIAL PRESSURE, ENHANCE CIRCULATION, AND ENCOURAGE SPONTANEOUS RESPIRATION

(75) Inventors: Anja Metzger, Stillwater, MN (US); Keith G. Lurie, Minneapolis, MN (US)

(73) Assignee: Advanced Circulatory Systems, Inc., Minneapolis, MN (US)

( * ) Notice: Subject to any disclaimer, the term of this patent is extended or adjusted under 35 U.S.C. 154(b) by 1050 days.

This patent is subject to a terminal disclaimer.

(21) Appl. No.: 12/141,864

(22) Filed: Jun. 18, 2008

(65) Prior Publication Data

US 2009/0020128 A1    Jan. 22, 2009

Related U.S. Application Data

(60) Provisional application No. 60/944,735, filed on Jun. 18, 2007.

(51) Int. Cl.  
*A61M 15/00* (2006.01)

(52) U.S. Cl. .......... 128/205.19; 128/207.16; 128/204.18

(58) Field of Classification Search ............. 128/204.18, 128/204.23, 204.26, 204.29, 205.19, 207.16  
See application file for complete search history.

(56) References Cited

U.S. PATENT DOCUMENTS

| | | | |
|---|---|---|---|
| 5,551,420 A | 9/1996 | Lurie et al. | |
| 5,692,498 A | 12/1997 | Lurie et al. | |
| 5,701,889 A * | 12/1997 | Danon | 128/204.29 |
| 5,730,122 A | 3/1998 | Lurie | |
| 5,881,725 A * | 3/1999 | Hoffman et al. | 128/204.26 |
| 6,029,667 A | 2/2000 | Lurie | |
| 6,062,219 A | 5/2000 | Lurie et al. | |
| 6,155,257 A | 12/2000 | Lurie et al. | |
| 6,224,562 B1 | 5/2001 | Lurie et al. | |
| 6,234,985 B1 | 5/2001 | Lurie et al. | |
| 6,312,399 B1 | 11/2001 | Lurie et al. | |
| 6,425,393 B1 | 7/2002 | Lurie et al. | |
| 6,459,933 B1 | 10/2002 | Lurie et al. | |
| 6,463,327 B1 | 10/2002 | Lurie et al. | |
| 6,526,973 B1 | 3/2003 | Lurie et al. | |
| 6,587,726 B2 | 7/2003 | Lurie et al. | |
| 6,604,523 B2 | 8/2003 | Lurie et al. | |
| 6,776,156 B2 | 8/2004 | Lurie et al. | |
| 6,863,656 B2 | 3/2005 | Lurie | |
| 6,935,336 B2 | 8/2005 | Lurie et al. | |

(Continued)

OTHER PUBLICATIONS

Lurie, K., et al., "Hyperventilation-induced hypotension during cardiopulmonary resuscitation," Circulation; Apr. 27, 2004; 109(16):1960-5.

*Primary Examiner* — Lynne Anderson  
(74) *Attorney, Agent, or Firm* — Kilpatrick Townsend & Stockton LLP

(57) ABSTRACT

Systems and methods are provided for decreasing intracranial pressure and enhancing circulation in a breathing person, as well as for increasing the respiratory rate and encouraging spontaneous respiration. According to such methods, a valve system is interfaced to a person's airway. The valve system has a threshold valve and an airway member that interfaces with the person's airway. The threshold valve is configured to prevent respiratory gas flow to the person's lungs during a portion of an inhalation event until the inspiration equals or exceeds an opening pressure of the threshold valve. Also, a small level of external vacuum is constantly supplied at a juncture between the threshold valve and the airway member.

26 Claims, 7 Drawing Sheets

U.S. PATENT DOCUMENTS

| | | |
|---|---|---|
| 6,938,618 B2 | 9/2005 | Lurie et al. |
| 6,986,349 B2 | 1/2006 | Lurie |
| 7,044,128 B2 | 5/2006 | Lurie |
| 7,082,945 B2 | 8/2006 | Lurie |
| 7,174,891 B2 | 2/2007 | Lurie et al. |
| 7,185,649 B2 | 3/2007 | Lurie |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,275,542 B2 | 10/2007 | Lurie et al. |
| 7,311,668 B2 | 12/2007 | Lurie et al. |
| 7,500,481 B2 * | 3/2009 | Delache et al. .......... 128/204.23 |
| 2004/0231664 A1 | 11/2004 | Lurie |
| 2005/0165334 A1 | 7/2005 | Lurie et al. |
| 2007/0221222 A1 | 9/2007 | Lurie |
| 2007/0277826 A1 | 12/2007 | Lurie |
| 2008/0047555 A1 | 2/2008 | Lurie et al. |
| 2008/0108905 A1 | 5/2008 | Lurie |
| 2009/0020128 A1 * | 1/2009 | Metzger et al. .......... 128/207.16 |

* cited by examiner

METHOD AND SYSTEM TO DECREASE INTRACRANIAL PRESSURE, ENHANCE CIRCULATION, AND ENCOURAGE SPONTANEOUS RESPIRATION

CROSS-REFERENCES TO RELATED APPLICATIONS

This application is a nonprovisional of, and claims the benefit of priority to, U.S. Provisional Patent Application No. 60/944,735 filed Jun. 18, 2007. This application is also related to U.S. patent application Ser. No. 12/119,374 filed May 12, 2008. The entire content of each of the above applications is incorporated herein by reference for all purposes.

BACKGROUND OF THE INVENTION

Embodiments of the present invention relate generally to the field of circulatory enhancement, and in particular to systems and methods for increasing blood circulation, decreasing intracranial pressure, lowering end tidal carbon dioxide, and increasing the respiratory rate in a spontaneously breathing patient.

Millions of people suffer life-altering and life-threatening consequences from any of a variety of medical conditions and disease states that impair circulation. These medical conditions and disease states range from one-time occurrences to chronic conditions, and include shock, traumatic brain injury, cardiac arrest, dehydration, kidney failure, congestive heart failure, wound healing, diabetes, stroke, respiratory failure, and orthostatic hypotension. The consequences of reduced circulation are severe and burden the health care system with billions of dollars of expenditures on an annual basis.

Despite recent advances in the field of circulatory enhancement, the need for improved approaches for treating patients with impaired circulation remains an important medical challenge. For example, there is an ongoing need for non-invasive techniques that enhance circulation of blood throughout the body, thereby increasing the opportunity for survival and the quality of life of patients who experience major medical emergencies and severe circulatory conditions. Embodiments of the present invention provide effective solutions to at least some of these needs.

BRIEF SUMMARY OF THE INVENTION

Embodiments of the present invention provide systems and methods for increasing circulation of blood flow in individuals with states of low blood flow or perfusion, such as those suffering from sudden cardiac arrest, shock, and other hypotensive conditions. Persons that are in shock due to a variety of reasons including trauma, dehydration, or sepsis may suffer from dangerously low blood pressure. Persons subjected to head trauma or stroke may suffer from elevated intracranial pressures. Such persons can benefit from interventions which increase their blood circulation, decrease their intracranial pressure, and increase their cerebral perfusion pressure.

Circulatory enhancement approaches disclosed herein are well suited for treating patients who are spontaneously breathing, for example, those receiving dialysis. Relatedly, such techniques can be beneficial in a plethora of clinical applications, including the treatment of cardiac arrest, intra-dialytic hypotension, dialysis, dehydration, diabetes, trauma and traumatic brain injury. Advantageously, these techniques can be used in any medical situation where an increase in circulation of blood is of benefit. Treatment embodiments can be administered by virtually anyone, from the layperson to the trained professional, and in any setting, including the home, a public venue, an ambulance, or a hospital. The medical systems and methods described herein can restore, maintain, or otherwise provide greater blood flow into the heart, resulting in increased cardiac output, which provides greater blood flow to the body's vital organs. Hence, these approaches can be used to restore life and improve the quality of life for patients suffering from cardiac arrest, low blood pressure, head injury, and the like.

Exemplary systems and methods provide non-invasive and instantaneous approaches for increasing the circulation of individuals in need thereof. In some instances, these techniques can use the body's biophysical performance to enhance circulation without the use of pharmaceutical or other mechanical agents. Often, treatment involves the use of a valve that selectively impedes inspiration during breathing. Inspiratory impedance can result in enhanced circulation, as evidenced by increased blood flow volume, cardiac output, and systolic blood pressure.

Techniques disclosed herein encompass systems and methods for providing safe, simple, and convenient treatment of low blood pressure in spontaneously breathing patients. For example, such techniques can be used to increase blood pressure during hypotension from a variety of causes, including, without limitation, orthostatic intolerance, hypovolemia, heat shock, dialysis, or blood donation. Embodiments of the present invention provide systems and methods for decreasing intracranial pressure and enhancing circulation in a breathing person, as well as for increasing the respiratory rate and encouraging spontaneous respiration. According to such embodiments, a valve system can be interfaced to a person's airway. The valve system can have a threshold valve and an airway member that interfaces with the patient's airway. The threshold valve can be configured to prevent or impede respiratory gas flow to the person's lungs during a portion of an inhalation event until the inspiration equals or exceeds an opening pressure of the threshold valve. Also, a small level of external vacuum can be supplied at a juncture between the threshold valve and the airway member. The external vacuum can be supplied continuously or intermittently as desired.

In one aspect, the opening pressure of the valve system is between about −7 cm $H_2O$ and −25 cm $H_2O$. The external vacuum level may be less than the opening pressure of the valve system and be in the range from about −1 cm $H_2O$ and −24 cm $H_2O$. In some aspects, embodiments provide systems to decrease intracranial pressure and enhance circulation in a breathing person, as well as to increase the respiratory rate and encourage spontaneous respiration. Systems can include a valve system that is configured to be coupled to a person's airway. The valve system can have a threshold valve and an airway member that interfaces with the patient's airway. The threshold valve can be configured to prevent respiratory gas flow to the person's lungs during a portion of an inhalation event until the inspiration equals or exceeds an opening pressure of the threshold valve. An external vacuum source can be configured to apply a small level of external vacuum at a juncture between the threshold valve and the airway member. The external vacuum can be supplied constantly or intermittently as desired.

In one aspect, the opening pressure of the valve system is between about −7 cm $H_2O$ and −25 cm $H_2O$. The external vacuum level may be less than the opening pressure of the threshold valve and be in the range from about −1 cm H2O and −24 cm $H_2O$. In one arrangement, a facial mask has a fitting for coupling to the external vacuum source, and the valve system and the fitting are incorporated into the facial mask. In another aspect, the external vacuum source includes an in-hospital vacuum, a suction pump, or a portable vacuum pump. As part of the methods, oxygen may be supplied through the valve system to supplement oxygen delivery to the patient during inhalation.

In another arrangement, the valve system includes a check valve, a spring valve, a duck valve, or other mechanical one-way valve. The external vacuum source in combination with the valve system may also serve to reduce end tidal carbon dioxide ($ETCO_2$) levels. In some cases, the method may remove secretions from the airway using the vacuum source.

In one aspect, embodiments of the present invention encompass medical methods for treating a breathing person, for example to decrease intracranial pressure and enhance circulation in the breathing person. Methods can include interfacing a valve system to a person's airway, where the valve system has a threshold valve and an airway member that interfaces with the person's airway, and the threshold valve is configured to prevent or impede respiratory gas flow to the person's lungs during a portion of an inhalation event until the inspiration equals or exceeds an opening pressure of the threshold valve. Methods can also involve supplying a small level of external vacuum at a location downstream of the threshold valve. In some cases, the external vacuum is supplied constantly. In some cases, the external vacuum is applied or in fluid communication with a juncture between the threshold valve and the airway member.

In another aspect, embodiments of the present invention encompass a system for treating a breathing person. Systems, which may decrease intracranial pressure and enhance circulation in a breathing person, can include a valve system that is configured to be coupled to a person's airway, where the valve system has a threshold valve and an airway member that interfaces with the person's airway. The threshold valve can be configured to prevent or impede respiratory gas flow to the person's lungs during a portion of an inhalation event until the inspiration equals or exceeds an opening pressure of the threshold valve. A system can also in clued an external vacuum source that is configured to apply a small level of external vacuum at a location downstream of the threshold valve.

In some aspects, embodiments encompass methods to increase the respiratory rate and encourage spontaneous respiration of a breathing person. Methods may include interfacing a valve system to a person's airway, where the valve system includes a threshold valve and an airway member that interfaces with the person's airway. The threshold valve may be configured to prevent respiratory gas flow to the person's lungs during a portion of an inhalation event until the inspiration equals or exceeds an opening pressure of the threshold valve. Methods may also include supplying a small level of external vacuum at a location downstream of the threshold valve.

In a further aspect, embodiments of the present invention encompass systems to increase the respiratory rate and encourage spontaneous respiration of a breathing person. Systems may include, for example, a valve system that is configured to be coupled to a person's airway. The valve system can have a threshold valve and an airway member that interfaces with the person's airway. The threshold valve may be configured to prevent respiratory gas flow to the person's lungs during a portion of an inhalation event until the inspiration equals or exceeds an opening pressure of the threshold valve. Systems may also include an external vacuum source that is configured to apply a small level of external vacuum at a location downstream of the threshold valve.

In some aspects, embodiments encompass medical devices for use in the treatment of a breathing person. A medical device can include, for example, a threshold valve, an airway member, and a vacuum port. A threshold valve can be configured to prevent or impede respiratory gas flow to the person's lungs during a portion of an inhalation event until the inspiration equals or exceeds an opening pressure of the threshold valve. An airway member can be in fluid communication with the valve. The airway member can be configured to interface with the person's airway. The vacuum port can be in fluid communication with the threshold valve, the airway member, or both. The vacuum port can be configured to transmit a vacuum from a vacuum source.

For a fuller understanding of the nature and advantages of the present invention, reference should be had to the ensuing detailed description taken in conjunction with the accompanying drawings.

DETAILED DESCRIPTION OF THE INVENTION

Embodiments of the present invention encompass systems and methods for enhancing circulation in a patient. These techniques are well suited for use in treating individuals that may suffer from or are at risk of developing a variety of clinical conditions due to low blood flow. For example, exemplary devices and methods can be used to treat subjects presenting sudden cardiac arrest, traumatic injury, heat stroke, fainting, and the like, which can result in or from states of low blood flow or perfusion. In such cases, a lack of adequate blood flow back to the heart can contribute to the low blood pressure. States of low blood flow can impair the body's circulatory function, which delivers oxygen to the body's vital organs and removes toxic cellular waste. Circulatory enhancement techniques disclosed herein can use inspiratory impedance to increase blood flow to the body's vital organs. Further, such approaches can enhance the body's biophysical performance without depending upon pharmaceutical or other outside agents. In many cases, these systems and methods can be used in spontaneously breathing patients to increase venous blood return to the heart.

Figure 1A:
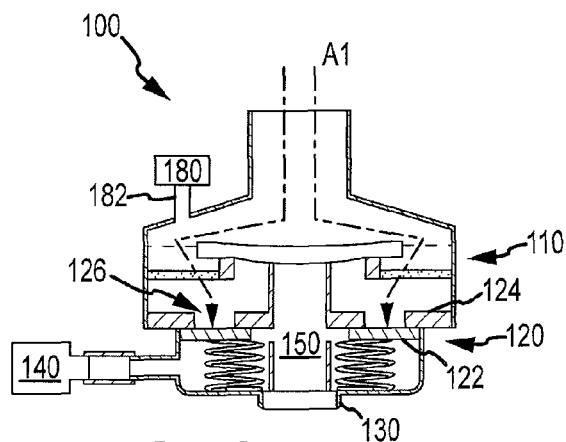
FIGS. 1A and 1B illustrate aspects of a circulatory enhancement system according to embodiments of the present invention.

Turning now to the drawings, FIG. 1A shows aspects of a circulatory enhancement system 100 according to embodiments of the present invention. Circulatory enhancement system 100 includes a valve system 110 that can be coupled with a person's airway. For example, valve system 110 may include a threshold valve 120 and an airway member 130 that interfaces with the patient's airway. Threshold valve 120 can be configured to prevent or impede respiratory gas flow to the person's lungs during a portion of an inhalation event until the inspiration equals or exceeds an opening pressure of the threshold valve. Circulatory enhancement system 100 may also include an external vacuum source 140 that is configured to constantly apply a small level of external vacuum at a juncture 150 between threshold valve 120 and airway member 130. As shown here, juncture 150 is disposed downstream of threshold valve 120, or otherwise downstream of the interface between diaphragm 122 and valve seat 124, and upstream of airway member 130. Valve seat 124 surrounds or defines an opening or passage 126 through which air or gas may flow when threshold valve 120 is in an open configuration. In the embodiment depicted here, diaphragm 122 is disposed against valve seat 124, and thus opening or passage 126 is closed. Vacuum source 140 operates to provide a small level of external vacuum that encourages inspiration. System 100 can be used to increase the respiratory rate and encourage spontaneous respiration of a patient. FIG. 1A illustrates a valve configuration where an inhalation event has been initiated, but the inspiration does not yet equal or exceed the opening pressure of the threshold valve, and hence the valve is closed. Hence, at the outset of the inhalation phase of a breathing cycle, the valve system prevents or impedes respiratory gases from flowing into the lungs until a threshold negative intrathoracic pressure level is met or exceeded. Air or gas flow, as depicted by arrow A1, does not travel past the threshold valve and toward the patient or person.

Figure 1B:
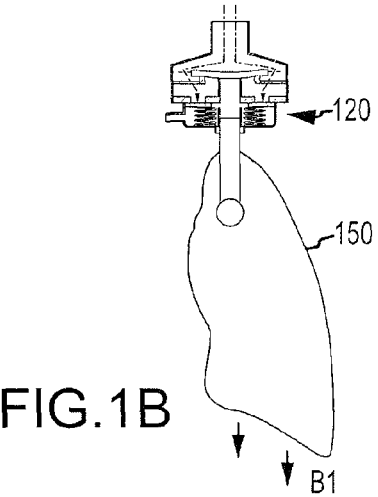

FIG. 1B schematically illustrates the physiological status of a patient corresponding to the valve configuration depicted in FIG. 1A. During inhalation as respiratory muscles are activated, the ribcage elevates and expands, and the diaphragm begins to contract downward pushing against the abdomen, as indicated by arrows B1. This requires work, and can be referred to as the active phase of respiration. When the size of the internal thoracic space or volume increases, there is a corresponding reduction in intrathoracic pressure (ITP). Hence, spontaneous inspiration and spontaneous inspiratory efforts can lead to a decrease in intrathoracic pressure. At this initial stage of a respiratory cycle, the valve 120 is in a closed configuration. Inspiration may have just begun, followed by a decrease in intrathoracic pressure. However, the intrathoracic pressure, in combination with or as supplemented by the external vacuum, is not sufficient to overcome the cracking limit of the valve, and thus the valve remains in the closed configuration and air is not freely flowing into the lungs 150. For example, the external vacuum may provide a pressure of about −4 cm $H_2O$ and the threshold valve may be set to open at an actuating pressure of about −12 cm $H_2O$.

Figure 2A:
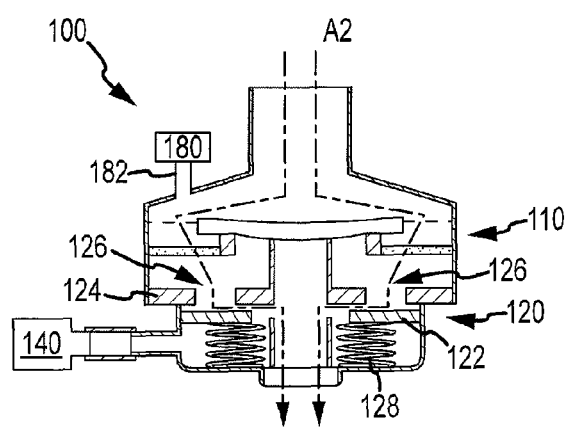
FIGS. 2A and 2B illustrate aspects of a circulatory enhancement system according to embodiments of the present invention.

FIG. 2A shows another configuration of circulatory enhancement system 100 as the inspiration equals or exceeds the opening pressure of the threshold valve. When the intrathoracic pressure, in combination with or as supplemented by the external vacuum, is sufficient to overcome the cracking limit of the valve, then the valve adopts an open configuration. Here, the open configuration of valve system 110 occurs during spontaneous inspiration or when the negative intrathoracic pressure within the chest exceeds the cracking pressure of the check valve. The sufficiently negative intrathoracic pressure or suction can draw air past the valve and into the lungs due to the resulting vacuum effect. The check valve is open and allows airflow to the patient. Hence, when the intrathoracic pressure level, in combination with or as supplemented by the external vacuum, exceeds the cracking pressure of the check valve 120, the diaphragm 122 of the check valve is pulled or moved downward or away from opening 126 and seat 124, as spring or resistance member 128 is compressed to permit respiratory gases to flow through openings 126 and to the patient's lungs 150. Check valve 126 may be set to open when the negative intrathoracic pressure is in the range from about 0 cm $H_2O$ to about −25 cm $H_2O$, optionally from about −2 cm $H_2O$ to about −20 cm $H_2O$. The setting of the check valve can be determined by the compressibility of resistance member 128, which may include a spring, elastomer, or other resilient mechanism. Hence, the magnitude and duration of negative intrathoracic pressure may be enhanced during patient inhalation by use of circulatory enhancement system 100. In this way, pressure within the venous blood vessels that transport blood out of the brain are also lowered. In so doing, more blood is drawn out of the brain to reduce intracranial and intraocular pressures. Air or gas flow, as depicted by arrow A2, travels past the threshold valve and toward and into the patient or person.

Figure 2B:
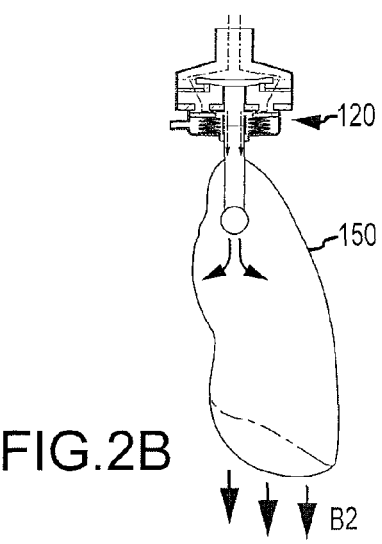

FIG. 2B schematically illustrates the physiological status of a patient corresponding to the valve configuration depicted in FIG. 2A. As inhalation continues, respiratory muscles are more fully activated, the ribcage continues to elevate and expand, and the diaphragm further contracts downward pushing against the abdomen. The growing size of the internal thoracic space or volume leads to further reduction in intrathoracic pressure (ITP). As the intrathoracic pressure, in combination with or as supplemented by the external vacuum, is sufficient to overcome the cracking limit of the valve, the valve 120 adopts an open configuration. For example, the external vacuum may provide a pressure of about −4 cm $H_2O$ and the threshold valve may be set to open at an actuating pressure of about −12 cm $H_2O$.

Figure 3A:
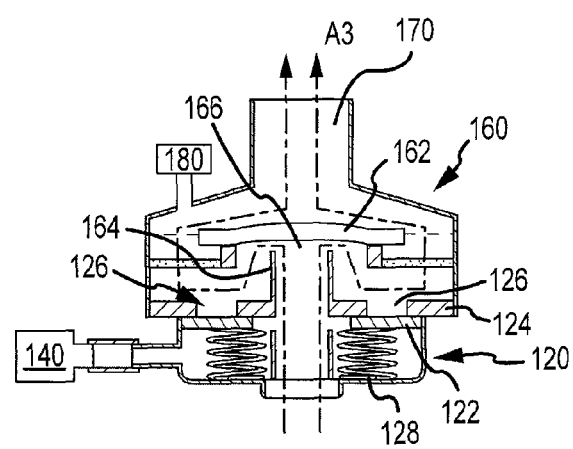
FIGS. 3A and 3B illustrate aspects of a circulatory enhancement system according to embodiments of the present invention.

FIG. 3A shows another configuration of circulatory enhancement system 100 as the inspiration becomes less than the opening pressure of the threshold valve. When the intrathoracic pressure, in combination with or as supplemented by the external vacuum, is no longer sufficient to overcome the cracking limit of the valve, then the valve adopts a closed configuration. Once the intrathoracic pressure falls below the threshold, recoil spring 128 again closes check valve 120 by forcing diaphragm against openings 126 and valve seat 124, thereby closing the openings. Here, the closed configuration of valve system 110 occurs during spontaneous exhalation or when the negative intrathoracic pressure within the chest no longer meets or exceeds the cracking pressure of the check valve. The check valve is closed and does not allow airflow to the patient, whereas an exhalation valve 160 can allow airflow out of the patient. Hence, during the exhalation phase of a breathing cycle, expired gases flow through the system 100, pressing against diaphragm 162 of exhalation valve 160, so as to move diaphragm 162 away from opening 166 and exhalation valve seat 164, and thereby open the exhalation valve. The gases flow past the exhalation valve and exit the system through opening 170. Air or gas flow, as depicted by arrow A3, travels past the threshold valve and away from or out of the patient or person.

Figure 3B:
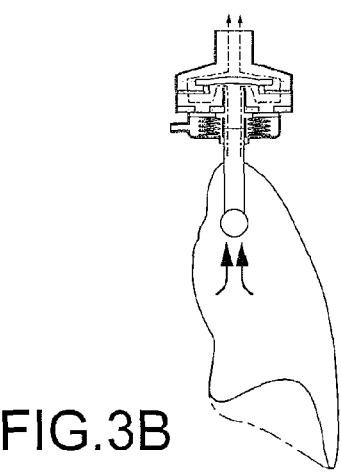

FIG. 3B schematically illustrates the physiological status of a patient corresponding to the valve configuration depicted in FIG. 3A. As inhalation ceases and expiration begins, respiratory muscles relax, the ribcage descends and contracts, and the diaphragm relaxes upward away from the abdomen. The decreasing size of the internal thoracic space or volume leads to an increase in intrathoracic pressure (ITP). As the intrathoracic pressure, in combination with or as supplemented by the external vacuum, is no longer sufficient to overcome the cracking limit of the valve, the valve adopts an closed configuration. Here, airflow is directed from the patient port toward the valve diaphragm. The diaphragm is pushed upward and air moves out through the ventilation port. In some cases, the external vacuum may provide a pressure of about −4 cm $H_2O$ and the threshold valve may be set to open at an actuating pressure of about −12 cm $H_2O$.

As indicated in FIGS. 1A, 1B, and 1C, circulatory enhancement system 100 may include a supplemental oxygen port 182 coupled with an oxygen source 180. The oxygen source and oxygen port can be used to supply supplementary oxygen to the patient's lungs. An external vacuum source 140 can be placed at or in fluid communication with a juncture between the valve system and the patient's airway, for example downstream of the threshold valve. In some cases, external vacuum source can be placed in fluid communication with any part of the circulatory enhancement system 100 or the patient airway that is downstream of the check valve or threshold valve. In some embodiments, a vacuum or negative pressure is applied downstream of the valve system or check valve via a lumen that is separate from the airway member 130. For example, in addition to interfacing airway member 130 with the patient's airway, it is also possible to interface a separate lumen with the patient's airway for the application of vacuum at a location downstream of the check valve. The vacuum source can provide a small level of external vacuum that encourages inspiration, thereby increasing the respiratory rate and the duration and magnitude of negative intrathoracic pressures generated during each inspiration. In this way, the vacuum can serve to enhance circulation and decrease intracranial pressures to a greater extent than without the external vacuum. The duration and magnitude of negative intrathoracic pressure can be increased in several ways. For example, because the patient may be breathing faster, for a given amount of time, the patient may experience more negative intrathoracic pressure than if breathing slower. Second, a continual vacuum can reduce or virtually eliminate the period during inspiration where nothing is happening in the airway (for example, where ITP=0). As such, the effective negative ITP can be much greater for each breathing cycle. Such features are illustrated in FIGS. 4 and 5.

Figure 4:
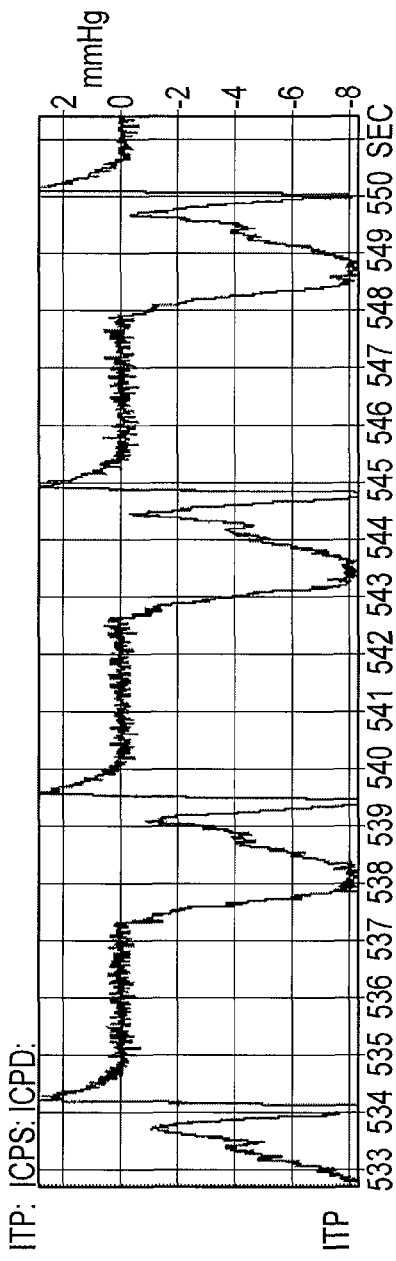
FIG. 4 illustrates a graph showing a subject's intrathoracic pressure (ITP) over various spontaneous breathing cycles when using a threshold valve, according to embodiments of the present invention.
Figure 5:
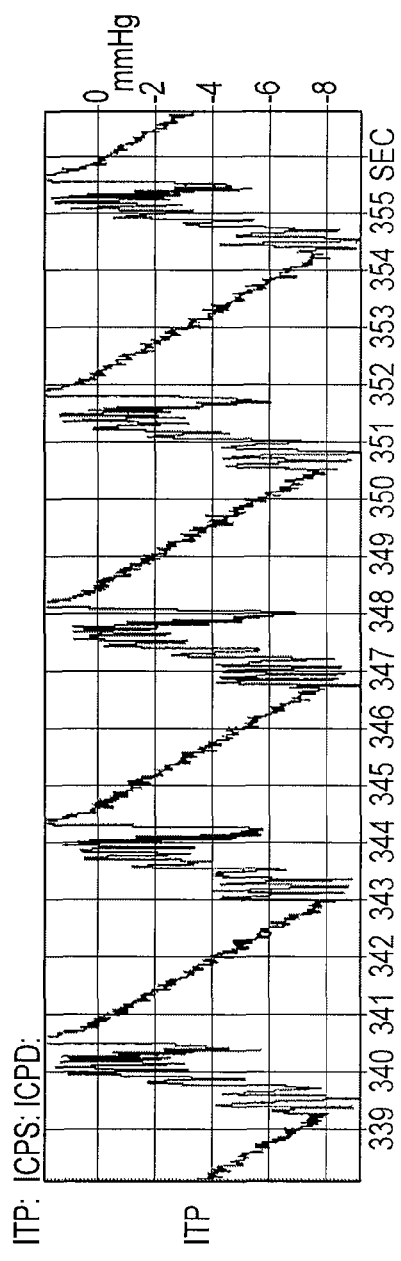
FIG. 5 illustrates a graph showing a subject's intrathoracic pressure (ITP) over various spontaneous breathing cycles when using a threshold valve and supplying a constant low level of vacuum downstream of the valve, according to embodiments of the present invention.

As shown in FIG. 4, the threshold valve can be set to open at a pressure of about −12 cm $H_2O$. This can result in the subject breathing at a rate of about 3.5 breaths per 18 seconds. In contrast, in the example of FIG. 5, a low level of vacuum is continuously supplied between the valve and the subject's airway. The threshold valve is set to open at the same actuating pressure as in FIG. 4 (i.e. about −12 cm $H_2O$), and the vacuum is supplied at a pressure of about −4 cm $H_2O$. As shown in FIG. 5, the subject is now breathing at a faster rate of about 5 breaths per 18 seconds. Also, right after the subject expires and the subject begins to inspire, the low level vacuum immediately begins to draw down the ITP as shown by the downwardly sloped diagonal line. Without the vacuum (as shown in FIG. 4), the ITP generally stays at 0 mmHg until the subject inspires enough to bring down the ITP. However, just as the ITP is significantly lowered, the valve opens and the ITP shoots back to 0 mmHg. Hence, the subject in FIG. 5 is at a negative ITP for much longer during the 18 seconds using the constant supply of vacuum than without.

In some options, an oxygen port on the valve system can be used to supply supplementary oxygen to the patient's lungs on a periodic basis. The external vacuum may suck up some of this oxygen but when the patient inhales, the inhalation can be forceful enough to allow the supplemental oxygen to enter the lungs.

Figure 6:
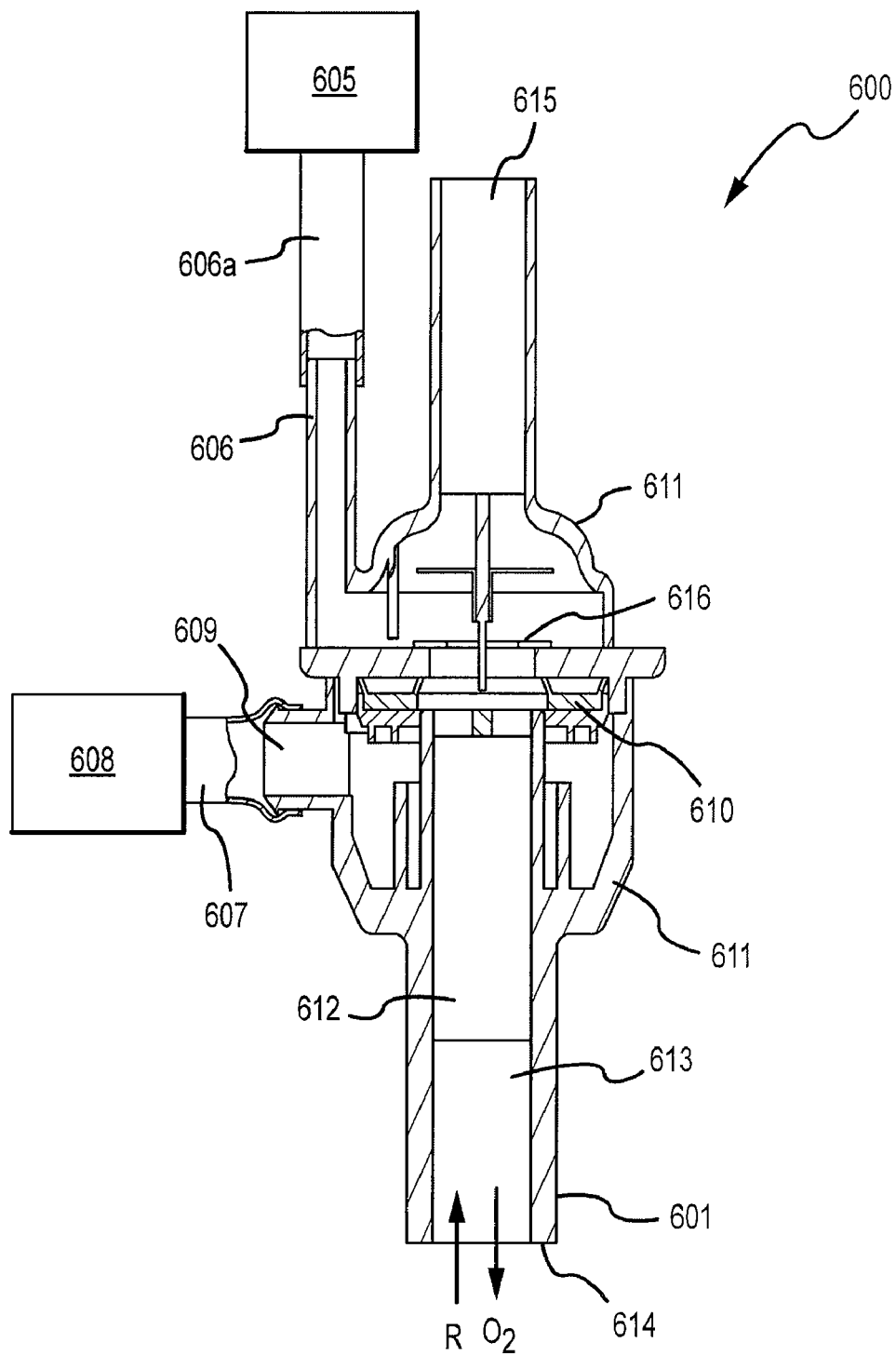
FIG. 6 illustrates aspects of a circulatory enhancement system according to embodiments of the present invention.

A system 600 suitable for the practice of embodiments of the invention is shown in FIG. 6. System 600 may include a housing 611 that defines or includes a central lumen 612. System 600 may also include a ventilation tube 601 having a central lumen 613 may be connected to or placed in fluid communication with the patient's respiratory system at its distal end 614. As used throughout the description provided herein, the term "ventilation tube" can refer to any patient connection or airway system having a central lumen through which respiratory gases may pass, e.g., an endotracheal tube, laryngeal mask airway device, supraglottic airway device, nasal masks, full face masks, lipseal mouthpieces, and the like. Typically, a ventilation tube provides a connection or passage to an airway of a patient or individual. Oxygen, optionally at high velocity, may be delivered into or through ventilation tube 601 through one or more tubules (cannulae) or passages that extend from $O_2$ source 605 into central lumen 612 through oxygen port or opening 606 and oxygen line 606a. Tubule(s) may run the length of ventilation tube 601 and direct a flow of high velocity $O_2$ into the patient's respiratory system at the distal tip 614 thereof, as shown by the arrow labeled "$O_2$". In some embodiments, the high velocity $O_2$ may be delivered at a velocity of between 20 and 1100 ft/sec and the diameter of tubules may be between 0.025-1.0 cm, depending upon the number of tubules used.

A vacuum line 607 connected to a vacuum source 608 may be coupled with or in communication with housing 611 via a vacuum regulation port 609. When activated, vacuum source 608 can generate a negative pressure or vacuum in lumen 612 and lumen 613 of ventilation tube 601, which results in or contributes to a negative intrathoracic pressure in the patient's airway and lungs, or otherwise reduces intrathoracic pressure in the patient's airway or lungs. This vacuum may help to generate or facilitate a flow of respiratory gases R from the patient's respiratory system into lumen 613 of ventilation tube 601 and lumen 612. An impedance threshold device or mechanism (ITD) 610 may be attached with housing 611 or otherwise included as part of system 600. ITD 610 may include a spring loaded valve that creates impeded inhalation. ITD 610 can operate to regulate or modulate gas flow between lumen 612 and ambient air inlet 615. In some embodiments, ITD 610 can include one or more features of an ITD that prevents or impedes respiratory gases R from flowing back into a patient's respiratory system thereby helping maintain a desired negative intrathoracic pressure. ITD 610 may be set to maintain a negative intrathoracic pressure between about −2 mmHg and about −20 mmHg. In some cases, ITD 610 may be set to maintain a negative intrathoracic pressure between about −6 mmHg and about −12 mmHg. Optionally, one or more gauges to assess changes in pressure within system 600 can be attached with or incorporated into system 600. Such gauge(s) may be used to provide the user with information regarding the pressure at various locations within system 600 at any point in time.

System 600 may be activated or operated by turning on $O_2$ source 605 and vacuum source 608 as soon as or after ventilation tube 601 is inserted into the patient's airway. In some cases, $O_2$ source 605 may be turned on before vacuum source 605. The continuous vacuum may be regulated by ITD 610, which can open at a preset cracking pressure, such that the intrathoracic pressure in the patient's respiratory system remains below atmospheric pressure, does not exceed a predetermined negative intrathoracic pressure value, or otherwise achieves a pressure as determined or desired by an operator or user. In some embodiments, the inspiratory resistance may never be greater that that to which ITD 610 is set. Thus, ITD 610 can serve to regulate the applied vacuum. In some embodiments, a means for delivering high velocity $O_2$ may be incorporated into the central lumen of a standard ventilator tube and may be separate from a means for applying the continuous vacuum. System 600 may also include a valve 616 that allows un-impeded exhalation.

Figure 7:
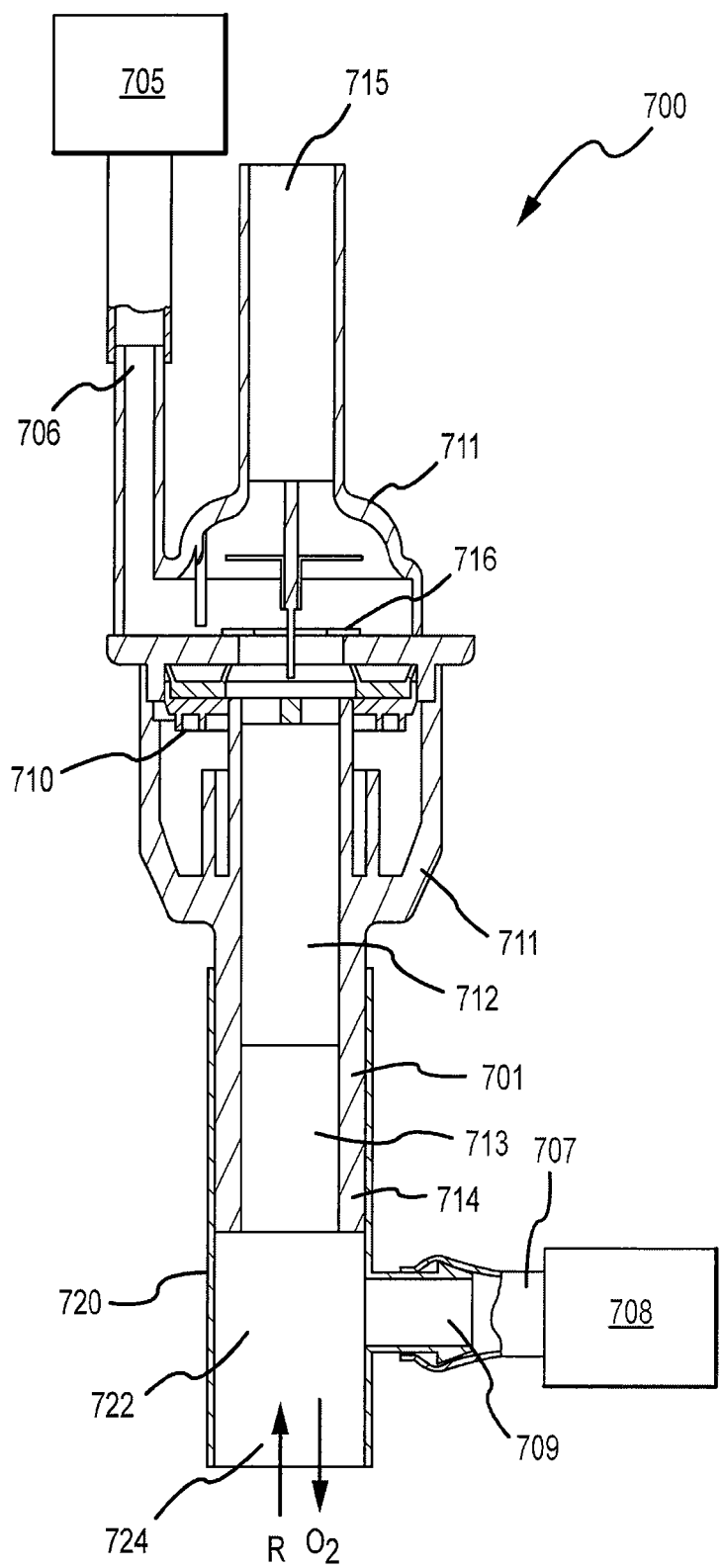
FIG. 7 illustrates aspects of a circulatory enhancement system according to embodiments of the present invention.

A system 700 suitable for the practice of embodiments of the invention is shown in FIG. 7. As depicted here, system 700 can include a distal vacuum connector piece that is not integral to the valve, but interfaces between the patient and the valve. The connector piece can include a vacuum port that can be coupled with a vacuum source. System 700 may include a housing 711 that defines or includes a central lumen 712. System 700 may also include a ventilation tube 701 having a central lumen 713 may be connected to or placed in fluid communication with the patient's respiratory system at its distal end 714, optionally via a vacuum connector piece 720 having a lumen 722. As used throughout the description provided herein, the term "ventilation tube" can refer to any patient connection or airway system having a central lumen through which respiratory gases may pass, e.g., an endotracheal tube, laryngeal mask airway device, supraglottic airway device, nasal masks, full face masks, lipseal mouthpieces, and the like. Typically, a ventilation tube provides a connection or passage to an airway of a patient or individual. Oxygen, optionally at high velocity, may be delivered into or through ventilation tube 701 through one or more tubules (cannulae) or passages that extend from $O_2$ source 705 into central lumen 712 through oxygen port or opening 706. Tubule(s) may run the length of ventilation tube 701 and direct a flow of high velocity $O_2$ into the patient's respiratory system, as shown by the arrow labeled "$O_2$". In some embodiments, the high velocity $O_2$ may be delivered at a velocity of between 20 and 1100 ft/sec and the diameter of tubules may be between 0.025-1.0 cm, depending upon the number of tubules used.

A vacuum line 707 connected to a vacuum source 708 may be coupled with or in communication with housing 711 via a vacuum regulation port 709 of interface connector 720. When activated, vacuum source 708 can generate a negative pressure or vacuum in lumens 712, 713, and lumen 722 of interface connector 720, which results in or contributes to a negative intrathoracic pressure in the patient's airway and lungs, or otherwise reduces intrathoracic pressure in the patient's airway or lungs. This vacuum may help to generate or facilitate a flow of respiratory gases R from the patient's respiratory system into lumen 722 of connector 720, and into lumens 713, 712. An impedance threshold device or mechanism (ITD) 710 may be attached with housing 711 or otherwise included as part of system 700. ITD 710 may include a spring loaded valve that creates impeded inhalation. ITD 710 can operate to regulate or modulate gas flow between lumen 712 and ambient air inlet 715. In some embodiments, ITD 710 can include one or more features of an ITD that prevents or impedes respiratory gases R from flowing back into a patient's respiratory system thereby helping maintain a desired negative intrathoracic pressure. ITD 710 may be set to maintain a negative intrathoracic pressure between about −2 mmHg and about −20 mmHg. In some cases, ITD 710 may be set to maintain a negative intrathoracic pressure between about −6 mmHg and about −12 mmHg. Optionally, one or more gauges to assess changes in pressure within system 700 can be attached with or incorporated into system 700. Such gauge(s) may be used to provide the user with information regarding the pressure at various locations within system 700 at any point in time.

System 700 may be activated or operated by turning on $O_2$ source 705 and vacuum source 708 as soon as or after a distal patient connection point 724 of connector 720 is inserted into or interfaced with the patient's airway. In some cases, $O_2$ source 705 may be turned on before vacuum source 705. The continuous vacuum may be regulated by ITD 710, which can open at a preset cracking pressure, such that the intrathoracic pressure in the patient's respiratory system remains below atmospheric pressure, does not exceed a predetermined negative intrathoracic pressure value, or otherwise achieves a pressure as determined or desired by an operator or user. In some embodiments, the inspiratory resistance may never be greater that that to which ITD 710 is set. Thus, ITD 710 can serve to regulate the applied vacuum. In some embodiments, a means for delivering high velocity $O_2$ may be incorporated into the central lumen of a standard ventilator tube and may be separate from a means for applying the continuous vacuum. System 700 may also include a valve 716 that allows un-impeded exhalation.

Figure 8:
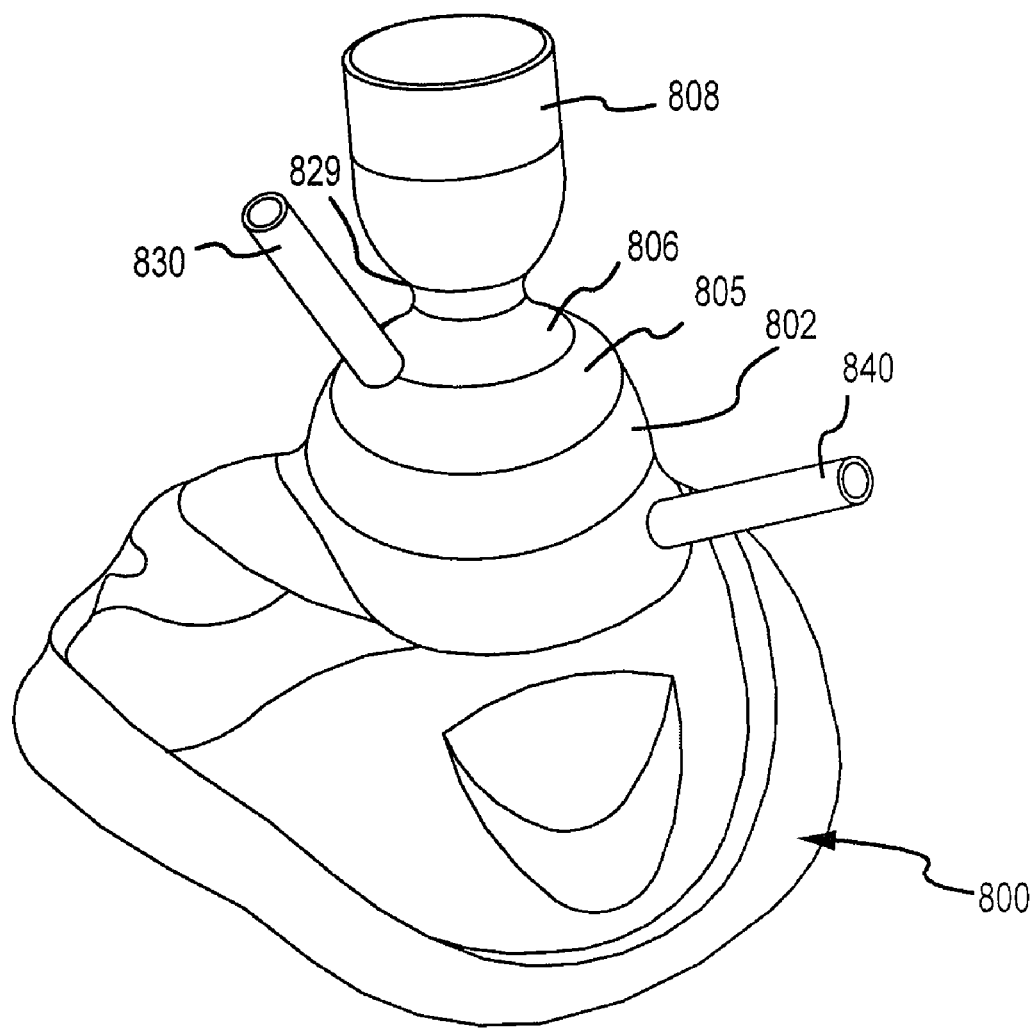
FIG. 8 illustrates aspects of a circulatory enhancement system according to embodiments of the present invention.

FIG. 8 illustrates an embodiment of a facial mask 800 to which is coupled a valve system 805. Mask 800 is configured to be secured to a patient's face so as to cover the mouth, nose, or both. Mask 800 and valve system 805 are examples of equipment that may be used to lower intrathoracic pressures and thereby lower intracranial and intraocular pressures. However, it will be appreciated that other valve systems and other coupling arrangements may be used. As such the invention is not intended to be limited to the specific valve system and mask described herein.

Figure 9:
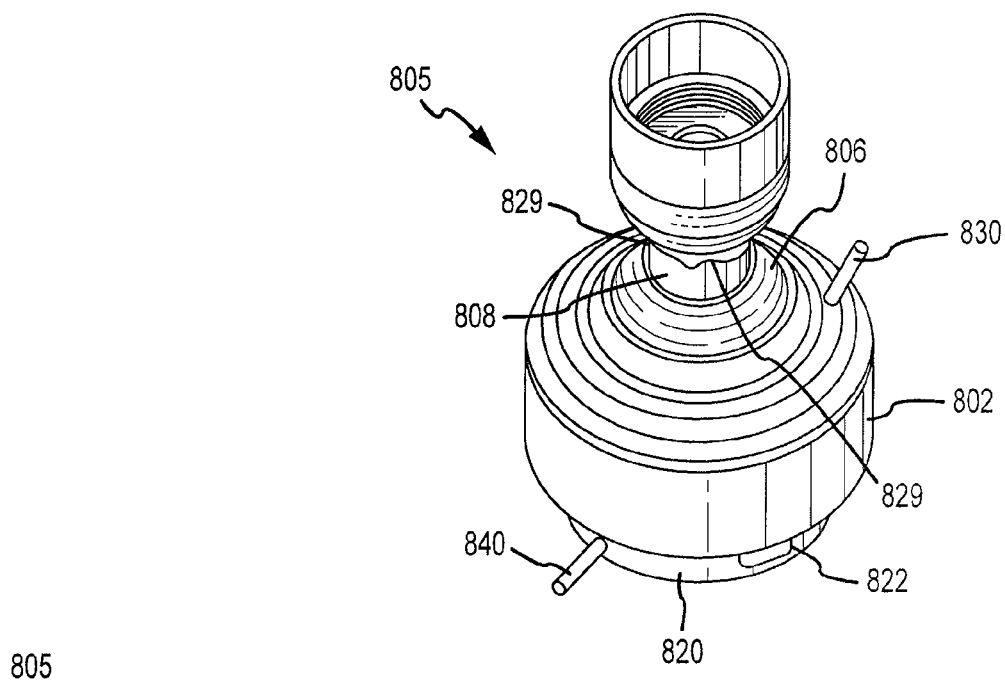
FIG. 9 illustrates aspects of a circulatory enhancement system according to embodiments of the present invention.
Figure 10:
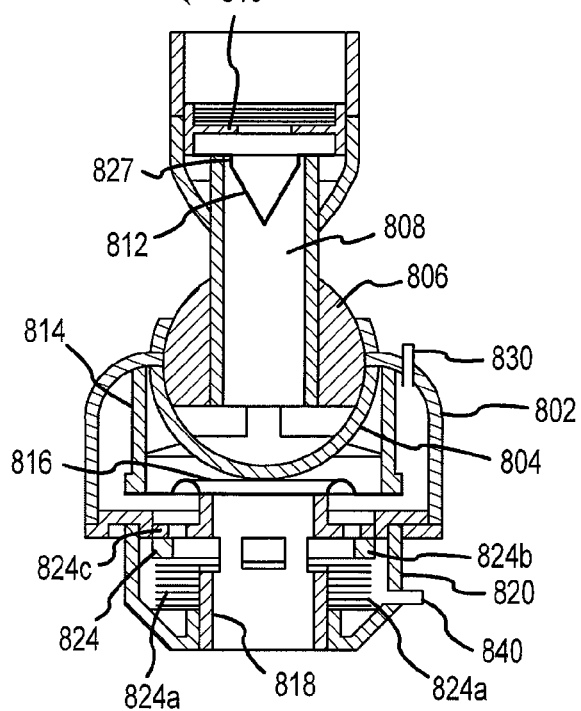
FIG. 10 illustrates aspects of a circulatory enhancement system according to embodiments of the present invention.
Figure 11:
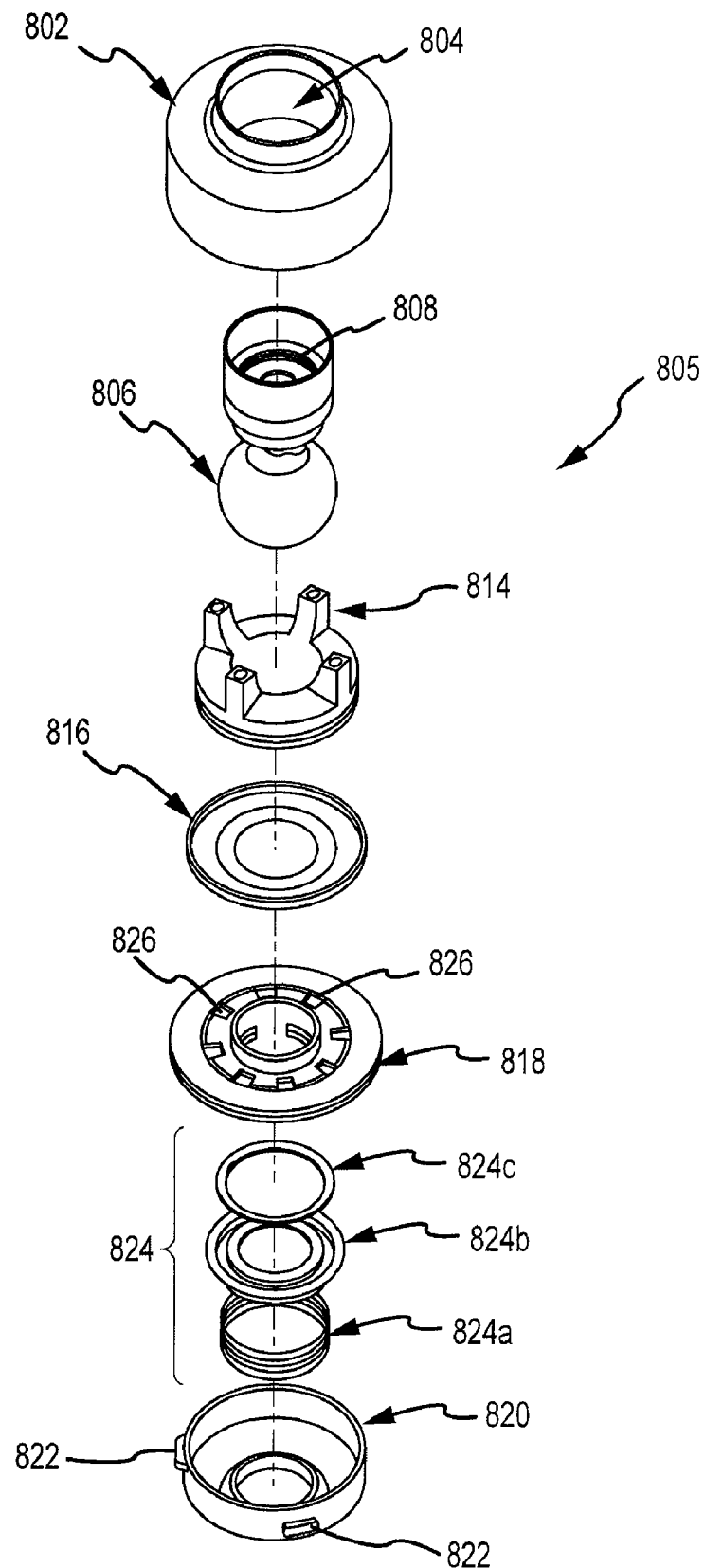
FIG. 11 illustrates aspects of a circulatory enhancement system according to embodiments of the present invention.

Referring also to FIGS. 9-11, valve system 805 will be described in greater detail. Valve system 805 includes a valve housing 802 with a socket 804 into which a ball 806 of a ventilation tube 808 is received. In this way, ventilation tube 808 may rotate about a horizontal axis and pivot relative to a vertical axis. A respiratory source, such as a ventilation bag, may be coupled to tube 808 to assist in ventilation. Disposed in ventilation tube 808 is a filter 810 that is spaced above a duck bill valve 812. A diaphragm holder 814 that holds a diaphragm 816 is held within housing 802. Valve system 805 further includes a patient port 818 that is held in place by a second housing 820. Housing 820 conveniently includes tabs 822 to facilitate coupling of valve system 805 with facial mask 800. Also held within housing 820 is a check valve 824 that comprises a spring 824a, a ring member 824b, and an o-ring 824c. Spring 824a biases ring member 824b against patient port 818. Patient port 818 includes bypass openings 826 that are covered by o-ring 824c of check valve 824 until the pressure in patient port 818 reaches a threshold negative pressure to cause spring 824a to compress.

When the patient is actively ventilated, respiratory gases are forced through ventilation tube 808. The gases flow through filter 810, through duck bill valve 812, and forces up diaphragm 816 to permit the gases to exit through port 818. Hence, at any time the patient may be ventilated simply by forcing the respiratory gases through tube 808. During the exhalation phase of a breathing cycle, expired gases flow through port 818 and lift up diaphragm 816. The gases then flow through a passage 827 in ventilation tube 808 where they exit the system through openings 829 (see FIG. 9). During the inhalation phase of a breathing cycle, valve system 805 prevents or impedes respiratory gases from flowing into the lungs until a threshold negative intrathoracic pressure level is exceeded. When this pressure level is exceeded, check valve 824 is pulled downward as springs 824a are compressed to permit respiratory gases to flow through openings 826 and to the patient's lungs by initially passing through tube 808 and duck bill valve 812. Valve 824 may be set to open when the negative intrathoracic pressure is in the range from about 0 cm $H_2O$ to about −25 cm $H_2O$, optionally from about −2 cm $H_2O$ to about −20 cm $H_2O$. Hence, the magnitude and duration of negative intrathoracic pressure may be enhanced during patient inhalation by use of valve system 805. Once the intrathoracic pressure falls below the threshold, recoil spring 824a again close check valve 824. In this way, pressure within the venous blood vessels that transport blood out of the brain are also lowered. In so doing, more blood is drawn out of the brain to reduce intracranial and intraocular pressures. As shown in FIGS. 8-10, valve system 805 can include a supplemental oxygen port 830 and a vacuum regulation port 840. Oxygen port 830 and vacuum regulation port 840 can operate in ways similar to those as described elsewhere herein, for example with reference to FIGS. 1A-3C, 6, and 7.

Embodiments encompass the use of a valve system that can be coupled to the patient's airway to regulate respiratory gas flows into the lungs. Such a valve system may include a threshold valve that prevents respiratory gases from flowing to the lungs until a certain amount of negative intrathoracic pressure (ITP), optionally in combination with or as supplemented by an external vacuum, is reached. At this point, the valve opens to permit gases to flow to the lungs. Valve systems according to embodiments of the present invention may incorporate features of valves such as those described in U.S. Pat. Nos. 5,692,498; 6,062,219; 6,526,973; and 6,604,523, incorporated herein by reference. However, it will be appreciated that a wide variety of threshold valve systems can be used. Such valve systems can be interfaced with a persons' airway to prevent respiratory gas flow to the person's lungs during a portion of an inhalation event to enhance circulation and decreases intracranial pressure, including those described in U.S. Pat. Nos. 6,986,349 and 7,195,012, incorporated herein by reference. Such valve systems enhance circulation by prolonging the duration and increasing the magnitude of negative intrathoracic pressure in the chest to increase venous return. By enhancing the amount of venous blood flow into the heart and lungs, cardiopulmonary circulation is increased. The intracranial pressure is decreased by facilitating the flow of cerebral spinal fluid from the head to the spinal cord and by lowering the intrathoracic pressures during inhalation to repetitively lower pressure in the venous blood vessels out of the head jugular and vertebral veins) to facilitate venous blood flow out of the head.

A variety of impeding or preventing mechanisms may be used to prevent or impede respiratory gases from flowing back into the lungs. Valve systems according to embodiments of the present invention may incorporate features of impeding or preventing mechanisms such as those described in U.S. Pat. Nos. 5,551,420; 5,692,498; 6,062,219; 5,730,122; 6,155,257; 6,234,985; 6,224,562; 6,986,349; and 7,204,251, the complete disclosures of which are herein incorporated by reference. The mechanisms may be configured to completely prevent or provide resistance to the inflow of respiratory gases into the patient while the patient inspires. In devices that completely prevent the flow of respiratory gases, the valves may be configured as pressure responsive valves that open after a threshold negative intrathoracic pressure has been reached, optionally in combination with or as supplemented by an external vacuum. Such systems and devices may be referred to herein collectively by the name "impedance threshold device" or "ITD". Valve systems according to embodiments of the present invention may incorporate features of ITDs such as those described in U.S. Pat. Nos. 6,526,973 and 6,604,523, incorporated herein by reference. However, it will be appreciated that a wide variety of devices may be used. As another example, devices may be interfaced with a person's airway to prevent respiratory gas flow to the person's lungs during a portion of an inhalation event to enhance circulation and decrease intracranial pressure, and may include features such as those described in U.S. Pat. No. 7,195,012, incorporated herein by reference.

Methods and devices, such as ITDs that reduce the amount of respiratory gases inside the thorax by preventing the gases from reentering the thorax during the chest wall recoil phase, or by actively removing said gases either intermittently or continuously, result in less and less air in the thorax. Less air in the thorax makes room for more and more blood to return to the heart during the chest wall recoil phase. Application of the methods and devices disclosed herein can cause a reduction in intrathoracic pressure during the chest wall recoil phase which results in a simultaneous decrease in intracranial pressures. As such, application of these methods and devices can increase circulation to the coronary arteries, increase blood flow to the brain, and enhance circulation throughout the body.

Embodiments of the present invention provide systems and methods for providing a continuous vacuum which may be applied to a patient's airway system. In some cases, the continuous vacuum may be applied for a period of time as desired by an operator or surgeon, or as may otherwise be determined beneficial to the patient. Embodiments may also include delivering or injecting an effective amount of $O_2$ gas into the person's lungs at a high velocity. Applying continuous vacuum to the patient's airway and simultaneously insufflating $O_2$ into the lungs at a high velocity sufficient to circulate $O_2$ the alveoli can provide enhanced blood flow to the heart and brain during or as part of a medical treatment.

In some embodiments, a continuous vacuum applied to patient may be about −2 mmHg to about −20 mmHg. In another embodiment, the velocity of the $O_2$-rich gas may be about 20 ft./sec. to about 1100 ft./sec. In still another embodiment, additional steps may be added wherein the continuous vacuum may be discontinued and positive or negative pressure ventilation may be supplied to the patient with or without the injection of high velocity oxygen gas.

In some embodiments, a continual negative intrathoracic pressure may be maintained at least in part by using an impedance threshold device that prevents respiratory gases from returning to the patient's thorax. In some embodiments, the delivery of $O_2$ gas and/or the application of continuous vacuum may be regulated based upon one or more physiological measurements such as airway pressure, intracranial pressure, $O_2$ saturation, end tidal $CO_2$, transcutaneous lactate, pH measurements, and the like.

A source of oxygen gas may be coupled with the valve system, which may be configured to inject an effective volume of oxygen gas from the source of oxygen gas into the patient's lungs at high velocity. Means may also be provided for applying a continuous vacuum to the person's airway simultaneously with the injection of oxygen gas and the performance of a level sufficient to maintain a continual negative intrathoracic pressure in the patient.

In some embodiments, the continuous vacuum is applied for at least 15 seconds and in some cases for at least 30 seconds. A vacuum means may include a source of continuous vacuum coupled with the valve system. An airway system may include or be coupled with a source of $O_2$, so that $O_2$ gas may be injected at high velocity into the person's airway during the application of continuous vacuum.

Exemplary methods may include interfacing an airway system with a patient's airway, where the airway system includes at least a first lumen and a second lumen; applying a continuous vacuum to the first lumen at a level sufficient to maintain a continual negative intrathoracic pressure in the patient; and injecting an effective volume of oxygen gas into the person's lungs at high velocity through the second lumen.

As used herein, including the appended claims, the term "patient" can mean any person or subject receiving a medical treatment or undergoing a medical procedure, and may include both human and non-human animals.

As used herein including the appended claims, the phrase "airway system" can include any system that is adapted to be interfaced with a patient's airway and has at least one lumen adapted to ventilate the patient's lungs, or is otherwise adapted to move or allow respiratory gases into and out of the patient's airway or lungs. Such airway systems are sometimes referred to herein as "airway adjuncts" or "ventilation tubes". Non-limiting examples of airway systems may include endotracheal tubes, supraglottic airway devices, Combitubes, obturator airways, laryngeal mask airways, and the like. Airway systems as described herein may also include at least a second lumen adapted to deliver oxygen gas into the patient's lungs.

In the context of at least some embodiments of the present invention, the combination of continuous high velocity $O_2$-rich gas delivery and the maintenance of a continuous application of a continuous vacuum to the patient's airway negative intrathoracic pressure may be viewed as optimizing or improving the blood circulation to the heart and brain. In addition, embodiments of the present invention may optimize the delivery of $O_2$ to and $CO_2$ removal from the patient's lungs.

As used herein, the phrases "continual negative intrathoracic pressure or vacuum" or "continuous negative intrathoracic pressure or vacuum" can mean a state in which, when optionally simultaneously combined the injection of high velocity $O_2$, application of vacuum or negative pressure to the patient's airway is not interrupted for any desired period of time. In some cases, the negative pressure can be applied for at least 15 seconds and in other cases at least 30 seconds, for example. The terms "negative pressure" or "vacuum" can refer to a pressure that is less than atmospheric pressure or less than about 760 mm Hg, according to some embodiments. In some cases, the term "negative intrathoracic pressure" refers to a pressure within the thorax, trachea, or intrathoracic cavity of a patient that is below atmospheric pressure; e.g. the intrathoracic pressure values are negative relative to atmospheric pressure. According to embodiments of the present invention, the terms "negative pressure" and "vacuum" may in some cases be used interchangeably. Continual or continuous negative intrathoracic pressure can refer to pressure within the intrathoracic cavity that continually remains below atmospheric pressure. In one embodiment of the invention, a continuous vacuum is applied to the patient's airway at a level sufficient to maintain a continual supplement to negative intrathoracic pressure in the patient and remove respiratory gases from the patient's airway. In some embodiments, the continuous vacuum may be applied to the patient's airway by connecting a vacuum source to the lumen of an airway system such as an endotracheal tube. In other embodiments, the continuous vacuum may be applied to the patient's airway by other means; e.g. through a connector for the vacuum source at a remote location in a ventilation circuit or through a separate lumen, such as a nasal tube. As described herein, the values of the negative intrathoracic pressure provided by the continuous vacuum may oscillate, but all of the values and therefore the intrathoracic pressures values may not remain continuously negative relative to atmospheric pressure. However, it is understood that the negative pressure (vacuum) applied to the patient's airway can remain continuously negative for a period of time, for example for at least 150 seconds, optionally during the injection of high velocity $O_2$.

The oxygen gas injected into the patient's lungs in accordance with embodiments of the invention is sometimes simply referred to herein, including the appended claims, as "$O_2$". It is understood that the term "$O_2$" is intended to include mixtures of oxygen and other gases. In some embodiments, the second lumen through which $O_2$ is delivered may be incorporated within the first lumen. For example, the first lumen may comprise the central lumen of a ventilation tube, e.g., an endotracheal tube, through which the second lumen may be disposed, and a continuous vacuum may be applied and maintained in the central lumen of the tube, e.g. through a valve mechanism or impedance threshold device.

In some embodiments of the invention, the volume of $O_2$ delivered via the second lumen is sufficient to result in adequate oxygenation of the alveoli of the lungs (sometimes referred to herein, including the appended claims, as an "effective volume" or an "effective $O_2$ volume"). In some embodiments, an effective $O_2$ volume may be in the range of about 1 liter to about 20 liters delivered to the lungs. Accordingly, these effective $O_2$ volumes may be referred to herein in units of "liters per minute" or "L/min". In some embodiments, an effective $O_2$ volume of between about 3 L/min and 15 L/min may be preferred. In some embodiments, an effective volume may be about 12 L/min. In some embodiments, the second lumen is positioned within the patient's airway so as to deliver an effective $O_2$ volume in close proximity to the patient's carina tracheae.

The velocity at which the effective $O_2$ volume is injected into the lungs in accordance with embodiments of the invention may be largely dependent on the diameter of the delivery lumen. In some embodiments, an effective $O_2$ volume may be delivered through one or more tubules having a lumen diameter small enough to generate what is sometimes referred to herein, including the appended claims, as a "high velocity" flow of $O_2$ or "high velocity $O_2$". As used herein, including the appended claims, the term "high velocity" can mean a velocity that is high enough to inject an effective $O_2$ volume into the patient's lungs without interfering with the generation and maintenance of continual negative intrathoracic pressure or a continuous vacuum in the patient's airway. In some embodiments, high velocity $O_2$ may have a velocity in the range of about 20 ft/sec to about 1100 ft/sec. In order to generate high velocity $O_2$, the diameter of the lumen delivering the effective $O_2$ volume may be in the range of about 0.1 cm to about 1.0 cm in some embodiment. In some embodiments, the lumen diameter may be about 0.25 cm to about 1.0 cm.

The injection of high velocity $O_2$ into the patient's lungs through the trachea may produce a laminar or turbulent flow pattern. The flow pattern may depend upon a number of factors including the volumetric flow rate, $O_2$ velocity, size of the one or more tubules used to inject the high velocity $O_2$, and the size and architectural characteristics of the receiving airway system. Optimizing the degree of laminar and/or turbulent flow patterns may help to improve the overall efficiency of the invention. For example, in some embodiments $O_2$ may be delivered as a high velocity $O_2$ laminar flow in one direction primarily in the middle of the trachea, bronchi, and bronchioles. As a result, the flow of gases in the reverse direction resulting from the applied vacuum may move closer to the walls of these structures. Accordingly, a simultaneous bidirectional exchange of respiratory gases can occur in a relatively efficient manner. Physiological feedback sensors that measure flow and pressure, for example, may provide a means to further optimize the flow characteristics and, thus, the efficiency of embodiments of the invention. Other physiological sensors may provide a similar kind of benefit.

Embodiments of the invention have now been described in detail for the purposes of clarity and understanding. However, it will be appreciated that certain changes and modifications may practiced within the scope of the appended claims.

What is claimed is:

1. A method to decrease intracranial pressure and enhance circulation in a breathing person, the method comprising:
    interfacing a valve system to an airway of the breathing person, the valve system having a threshold valve and an airway member that interfaces with the person's airway; and
    supplying a small level of external vacuum continuously throughout the breathing person's respiratory cycle at a location between the threshold valve and the breathing person's airway,
    wherein the threshold valve is configured to prevent or impede respiratory gas flow to the person's lungs during a portion of an inhalation event until the breathing person's intrathoracic pressure, in combination with the external vacuum, equals or exceeds an opening pressure of the threshold valve.

2. A method as in claim 1, wherein the external vacuum is supplied constantly at a juncture between the threshold valve and the airway member.

3. A method as in claim 2, wherein the external vacuum level is less than the opening pressure of the valve system and is between about $-1$ cm $H_2O$ and about $-24$ cm $H_2O$.

4. A method as in claim 1, wherein the opening pressure of the valve system is between about $-7$ cm $H_2O$ and about $-25$ cm $H_2O$.

5. A method as in claim 1, further comprising supplying oxygen through the valve system to supplement oxygen delivery to the patient during inhalation.

6. A method as in claim 1, wherein the external vacuum source in combination with the valve system serves to reduce end tidal carbon dioxide ($ETCO_2$) levels.

7. A method as in claim 1, further comprising removing secretions from the airway using the vacuum source.

8. A system to decrease intracranial pressure and enhance circulation in a breathing person, the system comprising:
    a valve system that is configured to be coupled to a person's airway, the valve system having a threshold valve and an airway member that interfaces with the person's airway; and
    an external vacuum source that is configured to apply a small level of external vacuum continuously throughout the breathing person's respiratory cycle at a location between the threshold valve and the breathing person's airway,
    wherein the threshold valve is configured to prevent or impede respiratory gas flow to the person's lungs during a portion of an inhalation event until the breathing person's intrathoracic pressure, in combination with the external vacuum, equals or exceeds an opening pressure of the threshold valve.

9. A system as in claim 8, wherein the opening pressure of the valve system is between about $-7$ cm $H_2O$ and about $-25$ cm $H_2O$.

10. A system as in claim 9, wherein the external vacuum level is less than the opening pressure of the threshold valve and is in a range from about $-1$ cm $H_2O$ to about $-24$ cm $H_2O$.

11. A system as in claim 8, further comprising a facial mask having a fitting for coupling to the external vacuum source, and wherein the valve system and the fitting are incorporated into the facial mask.

12. A system as in claim 8, wherein the external vacuum source comprises an in-hospital vacuum, a suction pump, or a portable vacuum pump.

13. A system as in claim 8, wherein the valve system comprises a check valve, a spring valve, a duck valve, or other mechanical one-way valve.

14. A method to increase the respiratory rate and encourage spontaneous respiration of a breathing person, the method comprising:
    interfacing a valve system to an airway of the breathing person, the valve system having a threshold valve and an airway member that interfaces with the person's airway; and
    supplying a small level of external vacuum continuously throughout the breathing person's respiratory cycle at a location between the threshold valve and the breathing person's airway,
    wherein the threshold valve is configured to prevent or impede respiratory gas flow to the person's lungs during a portion of an inhalation event until the breathing person's intrathoracic pressure, in combination with the external vacuum, equals or exceeds an opening pressure of the threshold valve.

15. A method as in claim 14, wherein the opening pressure of the valve system is between about $-7$ cm $H_2O$ and about $-25$ cm $H_2O$.

16. A method as in claim 15, wherein the external vacuum level is less than the opening pressure of the valve system and is between about $-1$ cm $H_2O$ and about $-24$ cm $H_2O$.

17. A method as in claim 14, further comprising supplying oxygen through the valve system to supplement oxygen delivery to the patient during inhalation.

18. A method as in claim 14, wherein the external vacuum source in combination with the valve system serves to reduce end tidal carbon dioxide ($ETCO_2$) levels.

19. A method as in claim 14, further comprising removing secretions from the airway using the vacuum source.

20. A system to increase the respiratory rate and encourage spontaneous respiration of a breathing person, the system comprising:
    a valve system that is configured to be coupled to a person's airway, the valve system having a threshold valve and an airway member that interfaces with the person's airway; and
    an external vacuum source that is configured to apply a small level of external vacuum continuously throughout the breathing person's respiratory cycle at a location between the threshold valve and the breathing person's airway,
    wherein the threshold valve is configured to prevent or impede respiratory gas flow to the person's lungs during a portion of an inhalation event until the breathing person's intrathoracic pressure, in combination with the external vacuum, equals or exceeds an opening pressure of the threshold valve.

21. A system as in claim 20, wherein the opening pressure of the valve system is between about $-7$ cm $H_2O$ and about $-25$ cm $H_2O$.

22. A system as in claim 20, wherein the external vacuum level is less than the opening pressure of the threshold valve and is in a range from about −1 cm $H_2O$ to about −24 cm $H_2O$.

23. A system as in claim 20, further comprising a facial mask having a fitting for coupling to the external vacuum source, and wherein the valve system and the fitting are incorporated into the facial mask.

24. A system as in claim 20, wherein the external vacuum source comprises an in-hospital vacuum, a suction pump, or a portable vacuum pump.

25. A system as in claim 20, wherein the valve system comprises a check valve, a spring valve, a duck valve, or other mechanical one-way valve.

26. A medical device for use in the treatment of a breathing person, comprising:

a threshold valve;

an airway member in fluid communication with the valve, wherein the airway member is configured to interface with an airway of the breathing person; and a vacuum port in fluid communication with the threshold valve, the airway member, or both, wherein the vacuum port is configured to transmit a vacuum from a vacuum source, wherein the device is configured to allow a continuous supply of a small level of vacuum throughout the breathing person's respiratory cycle at a location between the threshold valve and the breathing person's airway, and wherein the threshold valve is configured to prevent or impede respiratory gas flow to the person's lungs during a portion of an inhalation event until the breathing person's intrathoracic pressure, in combination with the external vacuum, equals or exceeds an opening pressure of the threshold valve.

* * * * *